United States Patent [19]
Asakura et al.

[11] Patent Number: 6,037,147
[45] Date of Patent: Mar. 14, 2000

[54] CYTOCHROME C AND POLYNUCLEOTIDES ENCODING CYTOCHROME C

[75] Inventors: Akira Asakura, Fujisawa; Tatsuo Hoshino; Masako Shinjoh, both of Kamakura; Noribumi Tomiyama, Fujisawa, all of Japan

[73] Assignee: Roche Vitamins Inc., Nutley, N.J.

[21] Appl. No.: 09/052,830

[22] Filed: Mar. 31, 1998

[30] Foreign Application Priority Data

Apr. 4, 1997 [EP] European Pat. Off. ............. 97105583

[51] Int. Cl.⁷ .......................... C12N 15/00; C12N 15/63; C12N 15/85; C12P 21/00; C07H 21/04
[52] U.S. Cl. .................. 435/69.1; 435/70.1; 435/320.1; 435/325; 536/23.1
[58] Field of Search .................. 536/23.1; 435/69.1, 435/320.1, 325, 70.1

[56] References Cited

U.S. PATENT DOCUMENTS 5,459,046  10/1995  Kodama et al. ................. 435/69.1

FOREIGN PATENT DOCUMENTS 606621  7/1994  European Pat. Off. .
832974  1/1998  European Pat. Off. .
WO 89/06688  7/1989  WIPO .

OTHER PUBLICATIONS

Curtuzzola et al. Biochemical Journal, vol. 322, pp 35–42, Feb. 15, 1997.
Okkels et al., J. of Biol. Chem., vol. 267, pp 21139–21145, Oct. 1992.
Matsushita, et al. FEMS Microbiol. Lett. 10, pp. 267–270 (1981).
Matsushita, et al. B.B.A. 894, pp. 304–312 (1987).
Ameyama et al. Agric. Biol. Chem. 51: pp. 2943–2950 (1987).
Takeda et al. J. Ferment. Bioeng. 74, pp. 209–213 (1992).
Hoshino, et al. Agric. Biol. Chem. 54(5) pp. 1211–1218 (1990).
Inoue I., et al. Bacteriol. 171 pp. 3115–3122 (1989).

*Primary Examiner*—Lisa B. Arthur
*Assistant Examiner*—Jehanne Souaya
*Attorney, Agent, or Firm*—Mark E. Waddell; Stephen M. Haracz; Bryan Cave LLP

[57] ABSTRACT

This invention is directed to cytochrome $c_{551}$ polypeptides and polynucleotides encoding the polypeptides.

35 Claims, 4 Drawing Sheets

PEPTIDE SEQUENCES DETERMINED WITH NATURAL CYTOCHROME $c_{551}^{II}$

PEPTIDE I:

LysTyrAlaAspLysProLeuLeu<u>AspTyrPheAsnTyrThrArgAspAsnMetProMetGlyAla</u>
                        c1

PEPTIDE II:

AlaAspThrAlaAlaThrGluGluAlaProAlaAlaAlaAlaGlyAlaAlaThrSerIleTyrAspGly
ValTyrThrAlaAlaGlnAlaGluAlaGly<u>GlnAlaAlaTrpMetThrSer</u>
                               c6

PEPTIDE III: <u>IleAsnAsnLysTyrAla</u>
             c5 c1, c5 AND c6: UNDERLINED SEQUENCES WERE USED FOR PREPARING OLIGONUCLEOTIDES
*: PEPTIDE III WAS LATER FOUND TO BE THE SEQUENCE AT THE HEAD OF PEPTIDE I.

FIG. 2A

OLIGONUCLEOTIDES SYNTHESIZED AS PROBES AND PRIMER

```
c1:   GATTATTTTAATTATAC
         C   C C C  C
c1R:  GTATAATTAAAATAATC
         G   G G G  G
c5:   ATTAATAATAAATATGC
         C C C  G   C
         A
c5R:  GCATATTTATTATTAAT
         G C  G   G
                  T
c6:   CAAGCTGCTTGGATGAC
         G C C
         A   A
         G   G
c6R:  GTCATCCAAGCAGCTTG
            G G    C
            T T
            C C
```

AADH-CYTOCHROME $c_{551}$ CONJUGATE WAS CONSTRUCTED IN IMITATION OF ALCOHOL DEHYDROGENASE (ADH) OF A. aceti HAVING CYTOCHROME c-like SEQUENCE IN ITS C-TERMINAL.

*1: SEQUENCE BETWEEN DEHYDROGENASE DOMAIN AND CYTOCHROME c DOMAIN OF ADH (PALNNRGFLPVKPP CORRESPONDING TO AMINO ACIDS 582 THROUGH 595 OF MATURE ADH) WAS USED AS A LINKER TO CONNECT AADH DOMAIN WITH CYTOCHROME $c_{551}$ DOMAIN.

*2: RESTRICTION SITES, Nhe I AND Bam HI, WERE INTRODUCED TO LIGATE THE THREE PARTS (AADH, LINKER, AND CYTOCHROME $c_{551}$).

FIG. 4

CYTOCHROME C AND POLYNUCLEOTIDES ENCODING CYTOCHROME C

BACKGROUND OF THE INVENTION

Cytochrome c is an essential component for mediating electron transfer between the primary dehydrogenases and the terminal oxidase for the oxidation of substrate with reduction of molecular oxygen to $H_2O$. This electron transfer reaction is based on an oxidation-reduction of the heme iron. Recently attempts have been made to apply the electron transfer reaction of cytochrome c as new materials imitating biological materials or elements, namely biochips; e.g. by using cytochrome $c_{552}$ of *Hydrogenobacter thermophilus* (Kodama et al., U.S. Pat. No. 5,459,046). Acetic acid bacteria including Gluconobacter and Acetobacter possess highly efficient ability for sugar- and sugar alcohol-oxidation and are industrially used for producing vinegar and L-sorbose which is used as intermediate of vitamin C production. In oxidative fermentation, cytochrome c plays an important role to complete the oxidation. Cytochrome c proteins have been purified and characterized from many organisms, including Gluconobacter; e.g. Matsushita et al. reported the purification of CO-binding cytochrome $c_{553}$ (CO) (molecular weight, 48 kDa) from *Gluconobacter suboxydans* (FEMS Microbiol. Lett., 10:267–270, 1981) and later the cytochrome $c_{553}$ (CO) was found to be identical to the second subunit of alcohol dehydrogenase of Gluconobacter. Amplification of the cytochrome $c_{553}$ (CO) in an alcohol dehydrogenase second subunit-deficient Gluconobacter slightly improved L-sorbose production from D-sorbitol in its specific rate (g-product per g-cell-hour) as disclosed in J. Ferment. Bioeng., 74, 209–213, 1992 (Y. Takeda et al.). In addition to the cytochrome $c_{553}$, cytochrome $c_{551}$(AL) (molecular weight 55 kDa) and cytochrome $c_{551}$(CO) (molecular weight 72 kDa) [Ameyama et al., Agri. Biol. Chem. 51, 2943–2950 (1987)] were also isolated from Gluconobacter. The cytochrome $c_{551}$(AL) is one of the subunits of aldehyde dehydrogenase of *Gluconobacter suboxydans* consisting of two subunits; the other subunit is primary aldehyde dehydrogenase of 86 kDa. AL in cytochrome $c_{551}$(AL) stands for "aldehyde".

SUMMARY OF THE INVENTION

This invention provides DNA sequences and polynucleotides which correspond to a newly isolated cytochrome $c_{551}$ that is one of the essential components mediating electron transfer between the primary dehydrogenase and the terminal oxidase. Accordingly, part of this invention is a polynucleotide comprising a DNA sequence selected from the group consisting of SEQ ID No. 1, a DNA sequence which is capable of hybridizing to SEQ ID No. 1, and a DNA sequence which encodes a polypeptide having the same amino acid sequence as the polypeptide encoded by SEQ ID No. 2 or encodes a polypeptide having the same amino acid sequence as the polypeptide encoded by a DNA sequence which is capable of hybridizing to SEQ ID No. 1.

A DNA sequence which is capable of hybridizing to SEQ ID No. 1 includes a sequence which is completely complementary to SEQ ID No. 1, and also includes sequences which hybridize under standard stringency conditions which are described in more detail below. Additional polynucleotides of this invention encode the cytochrome $c_{551}$ polypeptides and the fusion proteins described immediately below.

Also part of this invention are the cytochrome $c_{551}$ polypeptides. These include a polypeptide which is encoded by any of the above polynucleotide and a cytochrome $c_{551}$ which has the following characteristics: a molecular weight of about 18–20 kD by gel filtration and about 17–19 kD on SDS-PAGE, which when reduced has an alpha absorption maximum at 551 nm, a beta absorption maximum at 522 nm, and a gamma absorption maximum at 417 nm, which contains about 1 mole of heme per mole of protein, and which has an isoelectric point of about 3.95. Also part of this invention is a cytochrome $c_{551}$ which has the following characteristics: a molecular weight of about 18–20 kD by gel filtration and about 15.8–17.8 kD on SDS-PAGE, which when reduced has an alpha absorption maximum at 551 nm, a beta absorption maximum at 522 nm, and a gamma absorption maximum at 417 nm, which contains about 1 mole of heme per mole of protein, and which has an isoelectric point of about 3.75. These polypeptides may further include one, two, or all three of the specific amino acid sequences SEQ ID No. 3, SEQ ID No. 4, and SEQ ID No. 5. Also included are active fragments of the above polypeptides.

This invention includes a fusion protein which comprises any polypeptide of this invention, fused with an enzyme, preferably an alcohol aldehyde dehydrogenase.

Also part of this invention is a vector suitable for expression in a pro- or eukaryotic host cell comprising any polynucleotide of this invention, preferably a DNA sequence selected from the group consisting of SEQ ID No. 1, a DNA sequence which is capable of hybridizing to SEQ ID No. 1, and a DNA sequence which encodes a polypeptide having the same amino acid sequence as the polypeptide encoded by SEQ ID No. 2 or encodes a polypeptide having the same amino acid sequence as the polypeptide encoded by a DNA sequence which is capable of hybridizing to SEQ ID No. 1.

Host cells containing polynucleotides of this invention are contemplated, particularly the polynucleotide described immediately above. A host cell may be transformed by an expression vector containing the selected polynucleotide, or may have the polynucleotide integrated into its genome.

Such host cells may be of eukaryotic origin, preferably a mammalian or plant cell, or may be of prokaryotic origin. These host cells may in particular be obtained from bacteria, such as *Escherichia coli, Pseudomonas putida, Acetobacter xylinum, Acetobacter pasteurianus, Acetobacter aceti, Acetobacter hansenii,* and *Gluconobacter oxydans,* preferably *Gluconobacter oxydans* DSM No. 4025.

This invention is also directed to a process for producing cytochrome $c_{551}$, which comprises cultivating a host cell of this invention, particularly a host cell containing the preferred DNA sequence, in an appropriate culture medium and recovering the cytochrome $c_{551}$ from the culture medium.

DETAILED DESCRIPTION OF THE INVENTION

It is an object of the present invention to provide novel cytochrome c which belongs to a family of proteins which function as electron acceptors. More particularly, the novel cytochrome c of the present invention is useful as an electron acceptor for dehydrogenases such as alcohol and aldehyde dehydrogenase (AADH). The cytochrome $c_{551}$ of this invention differs from cytochrome $c_{553}$ (CO) [48 kDa], cytochrome $c_{551}$ (AL) [55 kDa], and cytochrome $c_{551}$ (CO) [72 kDa] in the following points:

in molecular weight; in their nucleotide sequences and amino acid sequences; and in function namely the cytochrome $c_{551}$ of the present invention is a better AADH electron acceptor. It is believed that the cytochrome $c_{551}$ of the present invention can function most effectively for the AADH electron acceptor among the cytochromes of Gluconobacter mentioned above in view of protein-protein interaction between a primary dehydrogenase and a cytochrome c.

The present invention is also directed to functional derivatives of the polypeptides of the present case. Such functional derivatives are defined on the basis of the amino acid sequences of the present invention by addition, insertion, deletion and/or substitution of one or more amino acid residues of such sequences wherein such derivatives still have cytochrome c activity measured by an assay known in the art or specifically described herein. Such functional derivatives can be made either by chemical peptide synthesis known in the art or by recombinant means on the basis of the DNA sequences as disclosed herein by methods known in the state of the art and disclosed e.g. by Sambrook et al. (Molecular Cloning, Cold Spring Harbour Laboratory Press, New York, USA, second edition 1989). Amino acid exchanges in proteins and peptides which do not generally alter the activity of such molecules are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

Any fragment of the polypeptides of this invention which is active, e.g. which has cytochrome c activity as determined by standard assays (or see Example 1(8)) is a polypeptide of this invention. Such fragments may be obtained from polypeptides of this invention by known physical and chemical methods for fragmenting proteins or by expression of partial DNA sequences such as SEQ ID NO. 1. Polypeptides of this invention may be modified by the addition of other moieties such as polyalkylene glycols (such as PEG) or other stabilizing moieties, and may be in the form of fusion proteins with selected portions of their own sequences, or with other polypeptides (whole or fragments) such as immunoglobulins or enzymes (for example AADH). Making fusion proteins is well within the skill of a practitioner of the art and may be done for example using DNA encoding the component proteins, or may be done by physical fusion of the component proteins. In addition, Example 6 shows how to make a fusion protein of this invention.

Purification of polypeptides of this invention is accomplished by a variety of methods known to a skilled person, as shown in Example 1. A purified polypeptide generally should provide a single band on gel electrophoresis. As an example, polypeptides of this invention may be isolated and purified from a cell free extract of disrupted cells, preferably from the soluble fraction of the microorganisms, by usual protein purification methods such as ammonium sulfate precipitation, dialysis, ion exchange chromatographies, gel filtration chromatographies, and affinity chromatographies.

Furthermore the present invention is directed to polynucleotides (DNA or RNA sequences) as described above. Generally such polynucleotides comprise a DNA sequence which encode upon expression in a pro- or eukaryotic host cell polypeptides having at least a part of the primary structure and one of the biological properties of cytochrome $c_{551}$ as disclosed, e.g. in the sequence listing as well as their complementary strands, or those which include these sequences, DNA sequences which hybridize, preferably under standard conditions with such sequences or fragments thereof and DNA sequences, which because of the degeneracy of the genetic code, do not hybridize under standard conditions with such sequences but which code for polypeptides having the same amino acid sequence.

The polynucleotides of this invention may also encode fusion proteins as described above. Making such polynucleotides is standard in the art and may be accomplished using the polynucleotides of this invention and a selected fusion partner such as AADH, whose sequence is known (European Patent Application No. 9611500.8). In addition, polynucleotides of this invention may include host/vector sequences added for purposes of cloning or expression. Polynucleotides of this invention may be obtained as described below using methods of DNA purification known to a skilled person. It is important to select as a DNA source a microorganism which has a cytochrome c capable of accepting electrons from a dehydrogenase, as may be determined by assays provided below. Gluconobacter strains are particularly useful.

"Standard conditions" for hybridization mean in this context the conditions which are generally used by a person skilled in the art to detect specific hybridization signals and which are described, e.g. by Sambrook et al., "Molecular Cloning" second edition, Cold Spring Harbour Laboratory Press 1989, New York, or preferably so called stringent hybridization and non-stringent washing conditions or more preferably so called moderately stringent conditions or even more preferably so called stringent hybridization and stringent washing conditions a person skilled in the art is familiar with and which are described, e.g. in Sambrook et al. (s.a.).

It is furthermore an object of the present invention to provide a polypeptide having cytochrome c activity and which is encoded by a DNA sequence defined above or a polypeptide having cytochrome c activity obtainable or obtained from a microorganism belonging to the genus Gluconobacter selected from the group consisting of cytochromes $c_{551}$ I and II which respectively show the following physicochemical properties:

(a) cytochrome $c_{551}$ I:
 (a) Molecular weight: about 19±1 kDa by gel filtration, and about 18.0±1.0 kDa by SDS-PAGE analysis,
 (b) Absorption spectrum: reduced form shows absorption maxima at 551 nm, 522 nm and 417 nm as alpha, beta and gamma peaks, respectively;

(c) Heme content: about 1 mol of heme/mol of protein;
(d) Isoelectric point: about 3.95;
and
(b) cytochrome $c_{551}$ II:
  (a) Molecular weight: about 19±1 kDa by gel filtration, and about 16.8±1.0 kDa by SDS-PAGE analysis;
  (b) Absorption spectrum: reduced form shows absorption maxima at 551 nm, 522 nm and 417 nm as alpha, beta and gamma peaks, respectively.
  (c) Heme content: about 1 mol of heme/mol of protein;
  (d) Isoelectric point: about 3.75

It is furthermore an object of the present invention to provide a DNA sequence as specified above further comprising a DNA sequence encoding a polypeptide having alcohol/aldehyde dehydrogenase activity. Such constructs can be prepared by methods described herein, (see Example 6).

It is furthermore an object of the present invention to provide a vector suitable for expression in a pro-or eukaryotic host cell comprising a DNA sequence as defined above and a host cell which has been transformed by such a vector, more specifically such a host cell in which host cell a DNA sequence as defined above has been integrated into its genome, furthermore such host cells which are of eukaryotic origin and preferably a mammalian or plant cell or such host cells which are of prokaryotic origin, especially when selected from the group consisting of bacteria, such as *Escherichia coli, Pseudomonas putida, Acetobacter xylinum, Acetobacter pasteurianus, Acetobacter aceti, Acetobacter hansenii,* and *Gluconobacter oxydans*, e.g. *Gluconobacter oxydans* DSM No. 4025.

In addition it is an object of the present invention to provide a process for producing cytochrome $c_{551}$, which comprises cultivating a host cell as defined above in an appropriate culture medium and recovering the cytochrome $c_{551}$ from the culture.

Cytochrome c of the present invention is also applicable for improving 2KGA production from L-sorbose or D-sorbitol and furthermore the production of aldehydees, carboxylic acids, and ketones from corresponding substrates in the presence of alcohol and aldehydee dehydrogenase in vivo and in vitro.

The compound 2KGA is an important intermediate for the production of ascorbic acid (vitamin C) into which it can be converted according to the well-known Reichstein method. The production of 2KGA from L-sorbose or from D-sorbitol by fermentation is known. Gluconobacter strains are known to produce 2KGA via the reaction catalyzed by sorbose and sorbosone dehydrogenases as disclosed in Agric. Biol. Chem., 54(5), 1211–1218, 1990 (T. Hoshino et al.) and in European Patent Publication No. 606621.

Therefore the use of cytochrome c of the present invention for the production of vitamin C is also an object of the present invention.

Before describing the present invention in more detail the physico-chemical properties of purified cytochrome $c_{551}$ consisting of isoforms, I and II, as obtainable from *Gluconobacter oxydans* are given below. These polypeptides are both encoded by the same polynucleotide.

(1) Molecular Weight

On the gel filtration of the purification step, the cytochromes $c_{551}$ I and II showed about 19±1 kDa apparent molecular weight. And, SDS-PAGE analysis showed molecular weights of 18.0±1.0 and 16.8±1.0 kDa for cytochromes $c_{551}$ I and II, respectively. Therefore, there are two cytochromes $c_{551}$ preparations showing close molecular weights and both cytochromes $c_{551}$ I and II are monomeric proteins.

(2) Absorption Spectrum and Heme Content

Figure 1A:
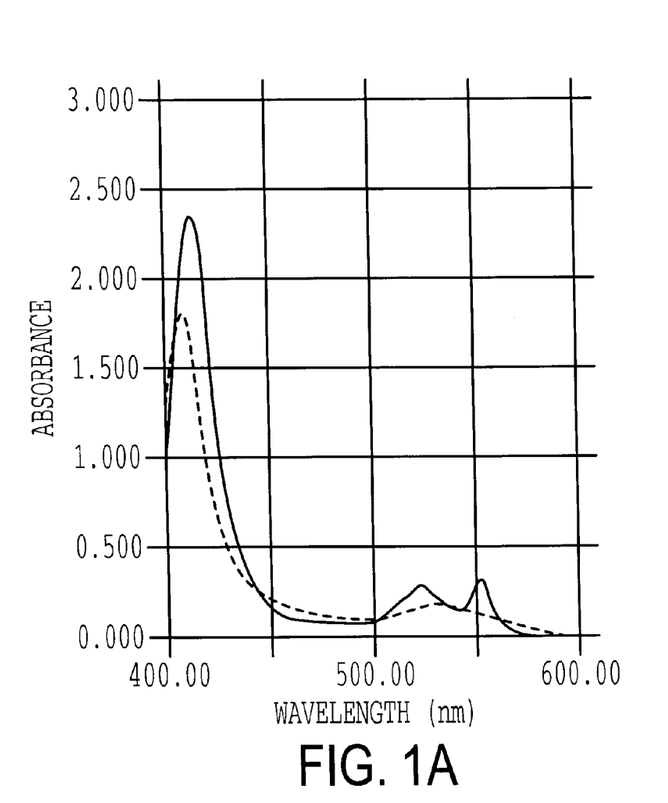
FIG. 1 shows an absorption spectrum of the cytochrome $c_{551}$ I and II. The protein concentration of the sample was each 0.4 mg/ml. Solid- and broken-lines are spectra of reduced- and oxidized-form, respectively.
Figure 1B:
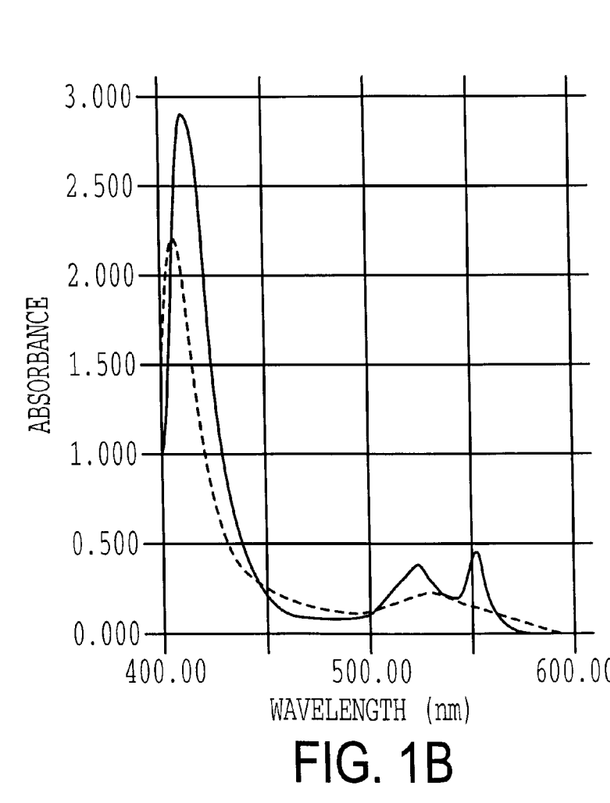

Absorption spectra of the cytochromes $c_{551}$ I and II which were fully reduced by addition of sodium dithionite are shown in FIG. 1. The spectra of both cytochromes $c_{551}$ I and II were indistinguishable from each other. The reduced cytochromes showed absorption maxima at 551 nm, 522 nm and 417 nm as alpha-, beta- and gamma peaks, respectively. And, oxidized cytochromes showed absorption maximum at 411 nm as a gamma peak. Heme contents of the cytochromes $c_{551}$ I and II were determined as about 1 mol/mol of protein, mono-heme, by the pyridine hemochrome method of Drabkin (J. Biol. Chem., 146: 605, 1942).

(3) Isoelectric Point

Isoelectric points (pI) were determined as 3.95 and 3.75 for the cytochromes $c_{551}$ I and II by the LKB (Stockholm, Sweden) isoelectric electrophoresis system, respectively.

(4) Peptide Mapping Comparison of the Cytochromes $c_{551}$ I and II

The cytochromes $c_{551}$ I and II were digested with V8 protease or thermolysin under the same condition, and peptide fragmentation patterns were compared by reverse-phase HPLC analysis. Major peptide fragmentation patterns (about 30 peptide fragment peaks) of the cytochromes $c_{551}$ I and II were identical, except that a few minor peptide fragment peaks were additionally observed on the cytochromes $c_{551}$ I and II, respectively. The result indicated strong amino acid sequence homology between the cytochromes $c_{551}$ I and II (5) Amino Acid Sequences of the Cytochrome $c_{551}$ II N-terminal amino acids of the cytochromes $c_{551}$ I and II were blocked by unknown modification. Therefore, internal amino acid sequences were determined from the peptide fragments. In addition to the V8 protease- and thermolysin-digested peptide fragments, the cytochrome $c_{551}$ II (heme removed and S-carboxylmethylated) was digested by lysyl-endopeptidase to make additional peptide fragments. Following internal amino acid sequences were determined with several peptide fragments obtained;

No. 1 (SEQ ID No. 3): AlaAspThrAlaAlaThrGluGluAla-ProAlaAlaAlaAlaGlyAlaAlaThrSerIleTyrAspGly Val-TyrThrAlaAlaGlnAlaGluAlaG-lyGlnAlaAlaTrpMetThrSerXaaAlaSerXaaHisGly ProThrAlaArgGlySer,

No. 2 (SEQ ID No. 4): GlyProArgValIleGlyProValIleA-snAsnLysTyrAlaAspLysProLeuLeuAspTyrPheAsn TyrThrArgAspAsnMetProMetGlyAlaProHisSerLeuSe rAspAspThrTyrValGlu,

No. 3 (SEQ ID No. 5): IleLeuGlnSerHisGlyAlaGluPro-GlyGluThrGlu.

The cytochrome c provided by the present invention can be prepared by cultivating an appropriate microorganism, disrupting the cells and isolating and purifying it from cell free extract of disrupted cells, preferably from the soluble fraction of the microorganism.

The microorganisms used in the present invention for isolating cytochrome c of the present invention belong preferably to the genus Gluconobacter which are capable of producing cytochrome c. Functional equivalents, subcultures, mutants and variants of said microorganism can be also used in the present invention. A preferred strain is *Gluconobacter oxydans*. A specific and preferred *Gluconobacter oxydans* strain has been deposited at the Deutsche Sammlung von Mikroorganismen in Göttingen (Germany) under DSM No. 4025 on Mar. 17, 1987. Moreover, a subculture of the strain has also been deposited in the Agency of Industrial Science and Technology, Fermentation Research Institute, Japan, under the stipulations of the Budapest Treaty under the deposit No.: *Gluconobacter oxydans* DSM No. 4025 FERM BP-3812 (date of deposit: Mar. 30, 1992). Furthermore, European Patent Publication 0278 477 discloses the characteristics of this strain.

The microorganisms may be cultured in an aqueous medium supplemented with appropriate nutrients under aerobic conditions. The cultivation may be conducted at pH between about 4.0 and 9.0, preferably between about 6.0 and 8.0. While the cultivation period varies depending upon pH, temperature and nutrient medium used, usually 2 to 6 days will bring about favorable results. A preferred temperature range for carrying out the cultivation is from about 13° to 36° C., preferably from about 18° to 33° C.

It is usually required that the culture medium contains such nutrients as assimilable carbon sources, digestible nitrogen sources and inorganic substances, vitamins, trace elements and the other growth promoting factors. As assimilable carbon sources, glycerol, D-glucose, D-mannitol, D-fructose, D-arabitol, L-sorbose, D-sorbitol and the like can be used.

Various organic or inorganic substances may also be used as nitrogen sources, such as yeast extract, meat extract, peptone, casein, corn steep liquor, urea, amino acids, nitrates, ammonium salts and the like. As inorganic substances, magnesium sulfate, potassium phosphate, ferrous and ferric chlorides, calcium carbonate and the like may be used.

In the following, embodiments for the isolation and purification of cytochrome c from the microorganisms after the cultivation and for its cloning of the gene/DNA sequence are described.

(1) Cells are harvested from the fermentation broth by centrifugation or filtration.

(2) The cells are suspended in the buffer solution and disrupted by means of a homogenizer, sonicator or treatment with lysozyme and the like to give a disrupted solution of cells.

(3) Cytochrome c is isolated and purified from a cell free extract of disrupted cells, preferably from the soluble fraction of the microorganisms by usual protein purification methods such as ammonium sulfate precipitation, dialysis, ion exchange chromatographies, gel filtration chromatographies, and affinity chromatographies.

The cytochrome c provided by the present invention is useful as an electron acceptor from an enzyme belonging to dehydrogenase for the production of aldehydees, carboxylic acids and ketones from alcohols and aldehydees, especially for the production of 2-KGA from L-sorbose or D-sorbitol via L-sorbosone.

Briefly, the cytochrome c gene, the DNA sequence, the recombinant expression vector and the recombinant organism, also called transformed host cell, utilized in the present invention can be obtained by the following steps:

(1) Isolating chromosomal DNA from the microorganisms which can provide cytochrome c that accepts electrons from dehydrogenases and constructing the gene library with the chromosomal DNA in *Escherichia coli.*

(2) Cloning cytochrome c gene from a chromosomal DNA by colony-, plaque-, or Southern-hybridization, PCR (polymerase chain reaction) cloning, Western-blot analysis and the like.

(3) Determining the nucleotide sequence of the cytochrome c gene obtained as above by usual methods to select DNA molecule containing said cytochrome c gene and constructing the recombinant expression vector on which cytochrome c gene can express efficiently.

(4) Constructing recombinant organisms carrying cytochrome c gene by transformation, transduction, transconjugation and electroporation.

The materials and the techniques used in the above aspect of the present invention are exemplified in details as follows:

A total chromosomal DNA can be purified by a procedure well-known in the art. The gene encoding cytochrome c is cloned in either plasmid or phage vectors from a total chromosomal DNA by the following methods:

(i) by determining the partial amino acid sequences from the purified cytochrome c by isolating the whole protein or peptide fragments obtained by peptidase-treatment from the gel after SDS-polyacrylamide gel electrophoresis and applying them to protein sequencer such as Applied Biosystems automatic gas-phase sequencer 470A (Perkin Elmer Corp., Norwalk, Conn., USA), synthesizing oligonucleotide probes with DNA synthesizer such as Applied Biosystems automatic DNA sequencer 381A (Perkin Elmer), according to the amino acid sequences obtained as above, isolating clones carrying the objective gene from a gene library of the strain carrying the objective gene with the oligonucleotide probes through Southern-, colony- or plaque-hybridization; (ii) by selecting clones expressing cytochrome c from the gene library by immunological methods with anti-cytochrome c antibody; or (iii) by amplifying the DNA from the total chromosomal DNA by PCR method with two oligonucleotides synthesized according to the amino acid sequences determined as above and isolating a clone carrying whole cytochrome c gene from the gene library constructed in *E. coli* by Southern-, colony-, or plaque-hybridization with the PCR product obtained above as the probe. Above mentioned antibody reacting against said cytochrome c can be prepared with purified cytochrome c protein or its peptide fragment by such method described in Methods in Enzymology, vol. 73, p 46, 1981.

The nucleotide sequence of the cytochrome c gene can be determined by a well known method such as dideoxy chain termination method with M13 phage (Sanger F. et al., Proc. Natl. Acad. Sci. USA, 74:5463–5467, 1977).

To express the cytochrome c gene or generally speaking the cytochrome c activity encoding DNA sequence efficiently, various promoters can be used; for example, the original promoter existing upstream of the the said cytochrome c gene, promoters of antibiotic resistance genes such as kanamycin resistant gene of Tn5 ( Berg, D. E., and C. M. Berg. 1983. Bio/Technology 1:417–435), ampicillin resistant gene of pBR322, and β-galactosidase of *E. coli* (lac), trp-, tac-, trc-promoter, promoters of lambda phage and any promoters which can be functional in the hosts consisting of microorganism including bacteria such as *Escherichia coli, Pseudomonas putida, Acetobacter xylinum, Acetobacter pasteurianus, Acetobacter aceti, Acetobacter hansenii,* and *Gluconobacter oxydans,* mammalian cells and plant cells.

For the object above other regulatory elements such as a Shine-Dalgarno (SD) sequence (for example, AGGAGG etc. including natural and synthetic sequences operable in the host cell) and a transcriptional terminator (inverted repeat structure including any natural and synthetic sequence operable in the host cell) which are operable in the host cell into which the coding sequence will be introduced and used with the above described promoter.

For the expression of periplasmic polypeptides, cytochrome c protein, a signal peptide, which contains usually 15 to 50 amino acid residues and are totally hydrophobic, is indispensable. A DNA encoding a signal peptide can be selected from any natural and synthetic sequence operable in the desired host cell.

A wide variety of host/cloning vector combinations may be employed in cloning the double-stranded DNA. Cloning vector is generally a plasmid or phage which contains an replication origin, regulatory elements, a cloning site including a multi-cloning site and selection markers such as antibiotic resistance genes including resistance genes for ampicillin, tetracycline, kanamycin, streptomycin, gentamicin, spectinomycin etc.

Preferred vectors for the expression of the object gene in *E. coli* are selected from any vectors usually used in *E. coli*, such as pBR322 or its derivatives including pUC18 and pBluescript II, pACYC177 and pACYC184 (J. Bacteriol., 134:1141–1156, 1978) and their derivatives, and a vector derived from a broad host range plasmid such as RK2 and RSF1010. A preferred vector for the expression of the object gene in Gluconobacter including *G. oxydans* DSM No. 4025 and *P. putida* is selected from any vectors which can replicate in Gluconobacter and/or *P. putida*, as well as a in preferred cloning organism such as *E. coli*. The preferred vector is a broad-host-range vector such as a cosmid vector like pVK102 and its derivatives and RSF1010 and its derivatives, and a vector containing a replication origin functional in Gluconobacter and another origin functional in *E. coli*. Copy number and stability of the vector should be carefully considered for stable and efficient expression of the cloned gene and also for efficient cultivation of the host cell carrying the cloned gene. DNA sequences containing transposable elements such as Tn5 can be also used as a vector to introduce the object gene into the preferred host, especially on a chromosome. DNA sequences containing any DNAs isolated from the preferred host together with the object gene are also useful to introduce the desired DNA sequence into the preferred host, especially on a chromosome. Such DNA sequences can be transferred to the preferred host by transformation, transduction, transconjugation or electroporation.

Useful hosts are of pro- or eukaryotic origin and may include microorganisms, mammalian cells, and plant cells. As a preferable microorganism, there may be mentioned bacteria such as *E. coli, P. putida, A. xylinum, A. pasteurianus, A. aceti, A. hansenii, G. oxydans*, and any Gram-negative bacteria which are capable of producing recombinant cytochrome c. Functional equivalents, subcultures, mutants and variants of said microorganism can be also used in the present invention. A preferred strain is *E. coli* K12 and its derivatives, *P. putida* or *G. oxydans* DSM No. 4025.

The DNA sequence encoding cytochrome c of the present invention is ligated into a suitable vector containing a regulatory region such as a promoter and a ribosomal binding site and transcriptional terminator operable in the host cell described above by well-known methods in the art to produce an expression vector.

To construct a host cell carrying an expression vector, various DNA transfer methods including transformation, transduction, conjugal mating (Chapters 14 and 15, Methods for general and molecular bacteriology, Philipp Gerhardt et al. ed., American Society for Microbiology, 1994), and electroporation can be used. The method for constructing a transformed host cell may be selected from the methods well-known in the field of molecular biology. Usual transformation system can be used for *E. coli*, Pseudomonas and Acetobacter. Transduction system can also be used for *E. coli*. Conjugal mating system can be widely used in Gram-positive and Gram-negative bacteria including *E. coli, P. putida* and *G. oxydans*. A preferred conjugal mating method was basically disclosed by the inventor in PCT Publication No. WO89/06688. The conjugation can occur in liquid medium or on a solid surface. The preferred recipient for cytochrome c production is selected from *E. coli, P. putida* and *G. oxydans*. The preferred recipient for 2KGA production is selected from *E. coli, P. putida* and *G. oxdans* which can produce active AADHs with a suitable recombinant expression vector. The preferred recipient for 2KGA production is *G. oxydans* DSM No. 4025. To the recipient for conjugal mating, a selective marker is usually added; for example, resistance against nalidixic acid or rifampicin is usually selected.

Cytochrome $c_{551}$ of the present invention can be used as a source for protein-protein conjugates such as AADH-cytochrome $c_{551}$ conjugates constructed with AADH encoding DNA sequences to improve total electron transfer efficiency as exemplified below.

The Examples which follow are provided to further illustrate the invention and are not intended to limit the invention in any way.

Example 1

Preparation of Cytochromes $c_{551}$ I and II

All operations were performed at 4° C. unless otherwise described.

(1) Cultivation of *G. oxydans* DSM No. 4025

A seed culture medium containing 8% L-sorbose (separately sterilized), 0.05% glycerol, 0.25% $MgSO_4.7H_2O$, 1.75% corn steep liquor, 5.0% baker's yeast, 0.5% $CaCO_3$, and 0.5% urea (separately sterilized), pH 7.0 was distributed into a test tube (5 ml each). Into the seed culture medium in test tube, one loopful amount of the cells of *G. oxydans* DSM No. 4025 grown on the NS2 plate agar medium containing 5.0% D-mannitol, 0.25% $MgSO_4.7H_2O$, 1.75% corn steep liquor, 5% baker's yeast (Oriental Yeast Co., Tokyo, Japan), 0.5% $CaCO_3$, 0.5% urea (separately sterilized), and 2.0% agar, pH 7.0 (before sterilization) at 27° C. for four days was inoculated and cultivated at 30° C. for 24 hr with shaking. The resulting seed culture was transferred into 100 ml of the same seed culture medium as described above in a 500 ml-Erlenmeyer flask and cultivated at 30° C. for 24 hr with 280 rpm rotating. Each 25 ml of the seed culture prepared as above was transferred into 500 ml of production medium containing 10% L-sorbose (separately sterilized), 0.05% glycerol, 1.6% urea (separately sterilized), 0.25% $MgSO_4.7H_2$, 6.25% baker's yeast cells, 1.5% $CaCO_3$ (production grade, nacaraitesque, Kyoto, Japan), and 3.0% corn steep liquor, pH 7.5 (before sterilization) in a 2000 ml-Erlenmeyer flask and cultivated at 30° C. for 35–40 hr with 180 rpm rotating. After the cultivation, solid materials such as baker's yeast cells and $CaCO_3$ were removed by low speed centrifugation (500×g, 15 min), twice. Then, *G. oxydans* DSM No. 4025 cells were harvested by centrifugation at 10,000×g for 15 min. The cells were resuspended in 25 mM Tris-HCl, 0.9% NaCl, 0.09% KCl, 10 mM $CaCl_2$, 5 mM $MgCl_2$, 5% sucrose, and 1 mM phenylmethylsulfanyl fluoride (PMSF), pH 8.0, and the cell suspension was centrifuged at 500×g for 15 min to remove solid materials, then the cells were collected by centrifugation at 10,000×g for 15 min and stored at −20° C. until use.

(2) Preparation of the Soluble Fraction

The cells obtained from 10 liter-culture (wet weight 40 g) were suspended with 60 ml of 25 mM Tris, 5 mM $CaCl_2$, pH 8.0 and disrupted by passing through French press (1500 kg/cm²) twice. DNase and MgCl₂ were added to the solution at the final concentration of 0.01 mg/ml and 1 mM, respectively, and cell debris was removed by centrifugation at 6,000×g for 10 min. From the cell free extract (8,800 mg total proteins) prepared as above, the soluble fraction containing cytochromes was separated by ultra-centrifugation at 100,000×g for 90 min and dialyzed against 25 mM Tris, 5 mM CaCl₂, pH 8.0.

(3) DEAE-Toyopearl 650M Column Chromatography

The soluble fraction was subjected to a column of DEAE-Toyopearl 650M (TOSOH Corp., Tokyo, Japan; 2.5 ID.×45 cm) which had been equilibrated with 25 mM Tris, 5 mM CaCl₂, pH 8.0. After washing the column with 400 ml of the same buffer, elution was carried out by a 2000 ml of 0–0.5 M NaCl linear gradient in the buffer. The deep red band showing 412 nm minus 480 nm difference absorption peak at around 0.13 M NaCl concentration was collected as the major cytochrome fraction.

(4) Butyl-Toyopearl 650S Column Chromatography

The major cytochrome fraction was diluted with the same volume of 25 mM Tris, 80% saturated $(NH_4)_2SO_4$, pH 8.0 with gentle stirring, centrifuged at 10,000×g for 15 min to remove insoluble materials and applied to a column of Butyl-Toyopearl 650S (TOSOH; 2.5 ID.×20 cm) which had been equilibrated with 25 mM Tris, 40% saturated $(NH_4)_2SO_4$, pH 8.0. After washing with 200 ml of the same buffer, elution was performed by 1000 ml of 40–0% saturated $(NH_4)_2SO_4$ linear gradient in the buffer. A cytochrome band which was eluted at around 20% saturated $(NH_4)_2SO_4$ concentration was collected and concentrated to 2.5 ml by using PM-10 ultrafilter under $N_2$ gas.

(5) Sephacryl S-100HR Gel Filtration

The cytochrome fraction was loaded onto a column of Sephacryl S-100HR (Pharmacia Biotech, Uppsala, Sweden; 2.5 ID.×90 cm) which had been equilibrated with 25 mM sodium-phosphate, 0.2 M NaCl, pH 7.2. The column was developed by the same buffer, and a cytochrome band showing about 19 kDa molecular weight was collected.

(6) Hydroxylapatite Column Chromatography

The major cytochrome fraction was extensively dialyzed against 0.2 mM sodium-phosphate/pH 6.8 and applied to the column of hydroxylapatite: HCA-100S (3.3×20 cm; Mitsui Toatsu chemicals Inc., Tokyo, Japan) which had been equilibrated with 0.2 mM sodium-phosphate (pH 6.8). After washing the column with 200 ml of the same buffer, elution was carried out by a 2000 ml of 0.2–18 mM sodium-phosphate (pH 6.8) linear gradient. During the gradient, the cytochromes were separated into two red bands and eluted. Therefore, the faster and later peaks were designated as the cytochromes $c_{551}$ I and II, respectively. Each cytochrome was dialyzed against 25 mM MOPS, 0.2 M NaCl/pH 7.5, concentrated to 2.0 ml by using PM-10 ultrafilter (Millipore Corp., Bedford, Mass., USA) under $N_2$ gas and stocked at −80° C. Finally, 37.4 mg of cytochrome $c_{551}$ I and 42.6 mg of cytochrome $c_{551}$ II were obtained from 8800 mg of total cell protein.

(7) Purity of the Cytochromes $c_{551}$ I and II

On the hydroxylapatite column chromatography (final purification step), each cytochrome was eluted as a single peak with constant absorption ratio of 280/410 nm. On SDS- and Native-PAGE analyses, each cytochrome showed a single protein band when it was stained or a visible red band when it was not stained. The molecular weights of cytochrome $c_{551}$ I and II were determined to be 18.0±1.0 and 16.8±1.0 kDa, respectively, by SDS-PAGE analysis.

(8) Electron Accepting Ability of the Purified Cytochromes $c_{551}$ I and II from the AADH of G. oxydans DSM No. 4025

The 2-KGA production system containing following defined and purified proteins was reconstituted. The system consisted of 12 μM AADH (purified from G. oxydans DSM No. 4025 by the method described by A. Asakura and T. Hoshino in European Patent Publication No. 606621), 14.4 μM cytochromes $c_{551}$ I and II (1:1 mixture), 250 μM horse heart type VI cytochrome c (purchased from Sigma, St. Louis, Mo., USA), 12.5 units/ml bovine heart cytochrome c oxidase type-aa3 (purchased from Sigma) and 50 mM MOPS buffer pH 7.5 containing 50 mg/ml L-sorbose, 5 mg/ml bovine serum albumin (fraction V, purchased from Sigma) and 0.2 M NaCl. In the 2-KGA production system, horse heart type VI cytochrome c and bovine heart cytochrome c oxidase type-aa3 catalyzed re-oxidation of bacterial cytochrome c, the cytochromes $c_{551}$ I and II, with oxygen reduction. After the reaction with aerobic incubation at 25° C. for 15 hours, about 8 mM of 2-KGA was accumulated. But, in the absence of the cytochromes $c_{551}$ I and II, 2-KGA accumulation was less than 0.2 mM. This cytochromes $c_{551}$ I and II-dependent 2-KGA production indicated the cytochromes $c_{551}$ I and II were effective electron acceptors for the 2-KGA producing catalytic cycle of AADH.

Example 2

Figure 2A:
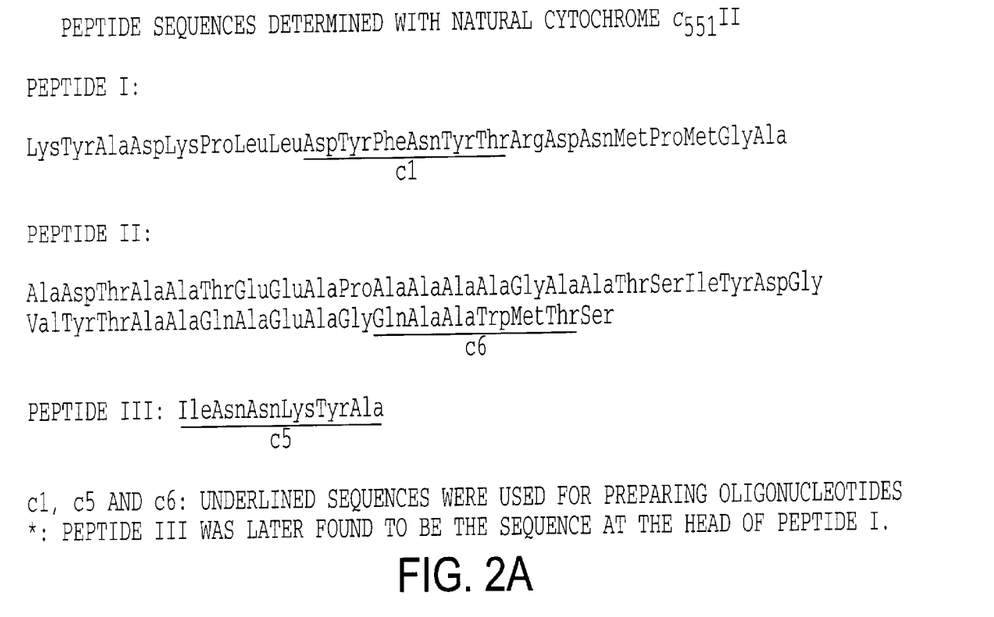
FIG. 2 shows sequences of peptides isolated from natural cytochrome $c_{551}$II and oligonucleotide synthesized.
Figure 2B:
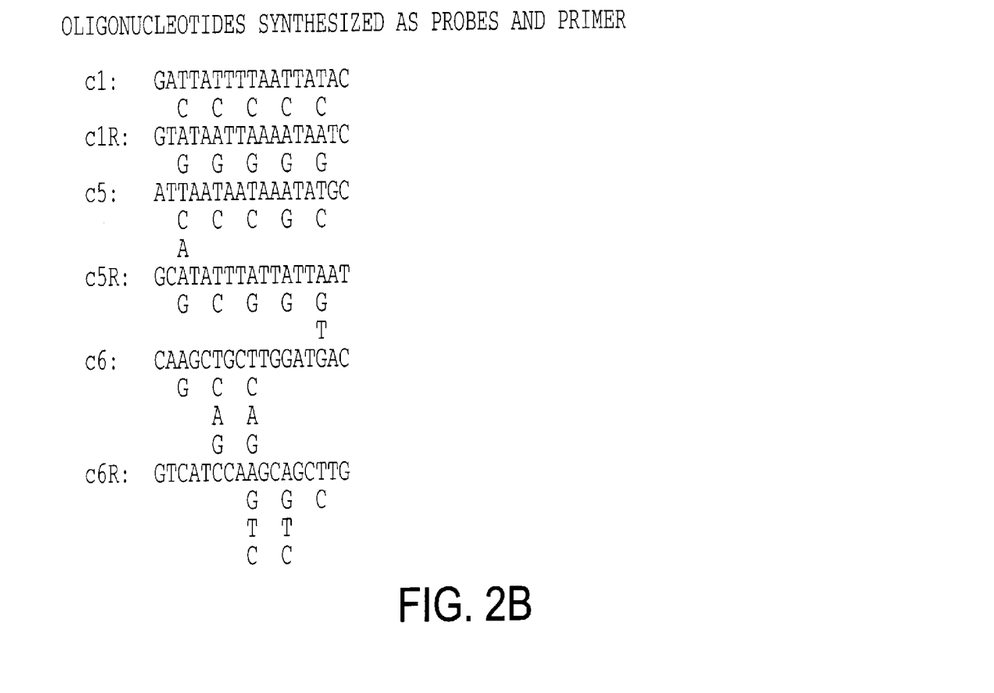

Cloning of Cytochrome $c_{551}$ Gene (1) Amplification of Partial Cytochrome $c_{551}$ Gene by PCR Method PCR was carried out using primers c1, c5, c6 and their antisense sequences (c1R, c5R, c6R), which were synthesized according to the amino acid sequences of the purified cytochrome $c_{551}$ protein with an Applied Biosystems 381A DNA synthesizer (USA) as shown in FIG. 2. The PCR reaction was carried out by using the GeneAmp™ DNA Amplification Reagent Kit (Takara Shuzo, Kyoto, Japan) with the Perkin-Elmer Cetus Instruments Thermal Cycler according to the recommendations of the supplier. The reaction consisted of 30 cycles of 1) denaturation step at 94° C. for 1 min; 2) annealing step at 48 or 40° C. for 2 min; and 3) synthesis step at 72° C. for 3 min. The reaction mixture (50 μl) contained 200 μM of dNTPs, 6.4 μM of each primer (32 degeneracy), 250 ng of chromosomal DNA of G. oxydans DSM No. 4025, and 2.5 u of Taq polymerase in the buffer supplied. When the PCR product was labeled with $^{32}P$, 0.74 MBeq of [α-$^{32}P$]dCTP and 40 μM of dCTP was added to the reaction mixture instead of 200 μM of dCTP. PCR with the primers, c5 and c1R, produced a 50 bp DNA, while PCRs with the other combination of primers produced no or many DNA bands.

(2) Cloning and Nucleotide Sequencing of the 50 bp DNA Fragment Amplified by PCR The 50 bp DNA fragment amplified by PCR was cloned into the Sma I site of pUC18 and sequenced by the dideoxy chain termination method (Proc. Natl. Acad. Sci. USA. 74:5463–5467, 1977). The determined nucleotide sequence of this 50 bp fragment was 5'-ATCAACAACAAGTATGCTGACAAGCCGCTGCTGG ACTACTTCAACTACAC-3' (SEQ ID No. 6.). The amino acid sequence deduced from this nucleotide sequence in the first frame (IleAsnAsnLysTyrAlaAspLysProLeuLeu AspTyrPheAsnTyrThr) includes the amino acid sequences (IleAsnAsnLysTyrAla, AspTyrPheAsnTyrThr) that were used for preparing primers.

(3) Southern-blot Analysis of the G. oxydans DSM No. 4025 Chromosomal DNA Using 50 Base-oligonucleotide as a Probe Southern blots prepared from the G. oxydans DSM No. 4025 chromosomal DNA digested with various restriction enzymes including EcoRI were probed by the 50-mer oligonucleotide that was synthesized by DNA synthesizer and labeled with $^{32}$P based on the sequence information of the 50 bases mentioned above. The probe hybridized only to 2.5 tb EcoRI fragment. This result indicates that cytochrome $c_{551}$ is produced from only one gene on the chromosomal DNA.

(4) Cloning of 2.5 kb EcoRI Fragment Containing Complete Cytochrome $c_{551}$-gene The chromosomal DNA of G. oxydans DSM No. 4025 was completely digested with EcoRI, and the resulting fragments were subjected to agarose gel electrophoresis. DNA fragments around 2.5 kb (2–3.5 kb) in size were cut out and eluted from the gel. The recovered DNA fragments were ligated with EcoRI-digested pUC 18 vector to transform E. coli JM109. About 1,000 transformants were obtained and screened by colony hybridization with the $^{32}$P-labeled 50-mer-oligonucleotide as a probe. Consequently, one colony showing a strong signal was obtained. Plasmid DNA was extracted from the colony and digested with EcoRI; its 2.5 kb EcoRI fragment showed a strong signal. The plasmid was designated as pGOC201. The 2.5 kb EcoRI fragment was also cloned in the vector, pVK100 (Knauf, V. C., et al., Plasmid 8:45–54, 1982), to generate the plasmids pGOC101 and pGOC101R, which have the 2.5 kb EcoRI fragment in opposite direction.

(5) Nucleotide Sequencing of Complete Cytochrome $c_{551}$ Gene

The nucleotide sequence of the cytochrome $c_{551}$ gene was determined by the dideoxy chain termination method. A 1.7 kb EcoRI-SmaI fragment was sequenced and one open reading frame (ORF of 507 bp existing in the sequence shown in SEQ ID No. 1) was found in the fragment. This ORF encodes a protein of 168 amino acids (SEQ ID No. 2), containing the three stretches consistent with the amino acid sequences of peptide fragments derived from the cytochrome $c_{551}$ digests (SEQ ID No. 3–5). The ORF also contained a typical signal sequence; the signal sequence is possibly cleaved after the ALA residues to generate the 25 residues of MetLysAsnLysThrThrLeuGlyGly-AlaLeuAlaLeuAlaAlaLeuLeuAlaGlyThrThrGlyAla LeuAla and the 143 residues of the mature sequence. The molecular weight of the mature cytochrome $c_{551}$ calculated from the sequence was 14,836. This value was somewhat smaller than the apparent molecular weights of cytochrome $c_{551}$ I & II (18,000 and 16,800) estimated with SDS-PAGE. In the middle of the mature protein (residues No. 51 to 55), CysAlaSerCysHis was found as a heme binding consensus sequence, CysXaaXaaCysHis.

(6) Subcloning of Cytochrome $c_{551}$ Gene by PCR Method

The 744 bp fragment containing the 117 bp-5'- and 120 bp-3'-flanking sequences of the ORF (507 bp) was amplified by PCR with primers tagged with the EcoRI site. The cloning of the amplified fragments into the vectors, pVK100 generated the plasmids pGOC102 and pGOC102R, which has the 744 bp fragment in opposite direction. The cloning of the 744 bp fragment into pMMB22 (Bagdasarian, M., et al., Gene 26: 273–282, 1983) generated the plasmid pGOC 402.

Example 3

Expression of Cytochrome $c_{551}$ Gene in E. coli, P. putida, and G. oxydans DSM No. 4025

(1) Expression of Cytochrome $c_{551}$ Gene in E. coli

Cell free extract of E. coli JM109 carrying pGOC402 or pMMB22 was subjected to Western-blot analysis. E. coli cells were grown in LB with 50 μg/ml of ampicillin overnight, and then 1% aliquots were inoculated into 5 ml of fresh medium. After 4 hours cultivation, the cultivation was continued for one more hour with or without addition of isopropyl-β-D-thiogalactopyranoside (IPTG) at a final concentration of 1 mM. Cells were harvested and suspended in water. After determining protein concentration, the cell suspension was diluted to a concentration of 2 mg protein/ml in Laemmli buffer consisting of 62.5 mM Tris-HCl (pH6.5), 10% glycerol, 2% SDS and 5% b-mercaptoethanol, and boiled for 3 min. Thirty μg of the cell free extracts was subjected to SDS-polyacrylamide gel (15%) electrophoresis. The resulting protein bands on the gel were blotted to a nitrocellulose filter with a semi-dry electroblotting apparatus (Trans-blot SD, Bio-Rad, Hercules, Calif., USA) operated at 25 V for 1 hour in 2.5 mM Tris-19.2 mM glycine buffer, pH 8.6, containing 20% methanol. The cytochrome $c_{551}$ protein was visualized by the treatment with anti-cytochrome $c_{551}$ antiserum, goat anti-rabbit IgG-horseradish peroxidase conjugate, hydrogen peroxide, and color developing reagents as recommended by the supplier (KONICA Co., Tokyo, Japan). The cells carrying pGOC402 prepared with or without IPTG -induction expressed two positive bands (about 30 ng or 10 ng of cytochrome $c_{551}$ in total per 30 μg cell free extract, respectively), whereas the cells carrying pMMB22 did not express them. The Rf values of these bands were identical with those of purified cytochrome $c_{551}$ I and II, indicating that cytochrome $c_{551}$ I and II are expressed from one gene and modified post-translationally or post-transcriptionally.

(2) Expression of Cytochrome $c_{551}$ gene in P. putida

At first, pGOC402 and pMMB22 were introduced into nalidixic acid resistant (Nal$^r$) P. putida ATCC 21812 by tri-parental conjugal mating method performed as follows. Cells of Nal$^r$ P. putida ATCC 21812 were cultivated at 30° C. in 5 ml of MB medium consisting of 2.5% mannitol, 0.5% yeast extract (Difco Laboratories, Detroit, Mich.) and 0.3% Bactotrypton (Difco). Donor strains, E. coli JM 109 carrying pGOC402 (streptomycin resistant: Sm$^r$) or pMMB22 (Sm$^r$), and a helper strain, E. coli HB101 carrying pRK2013 (Km$^r$, Figurski, D. H., Proc, Natl. Acad. Sci. USA 76: 1648–1652, 1979), were grown in LB medium containing appropriate antibiotics overnight at 37° C. These overnight cultures (2 ml each) were independently centrifuged and the cell pellets were independently suspended in 2 ml of MB medium. One hundred μl each of the cell suspensions were mixed and fifty μl of the mixed cell suspension were spotted onto a nitrocellulose filter placed on the surface of FB agar medium consisting of 5% fructose, 1% yeast extract (Difco), 1% Polypepton (Wako Pure Chemical Industries Ltd., Osaka, Japan) and 1.8% agar. The plate was incubated at 27° C. overnight. The resulting cells were spread onto MB agar medium containing 50 μg/ml nalidixic acid and 50 μg/ml streptomycin (MNS agar plate). The transconjugants thus obtained were purified by streaking on MNS agar plate to remove cells of E. coli and plasmid-free P. putida.

Cell free extract of P. putida transconjugant carrying pGOC402 or pMMB22 was prepared from the cells grown overnight in MB medium containing 50 μg/ml streptomycin with or without addition of 10 mM IPTG and subjected to Western-blot analysis as described in Example 3-1. The cells carrying pGOC402 prepared with or without IPTG-induction expressed two positive bands (about 30 and 10 ng of cytochrome $c_{551}$ in total per 20 μg cell free extract, respectively), whereas the cells carrying pMMB22 did not.

(3) Expression of Cytochrome $c_{551}$ gene in GOS2R and GORS6-35

Figure 3:
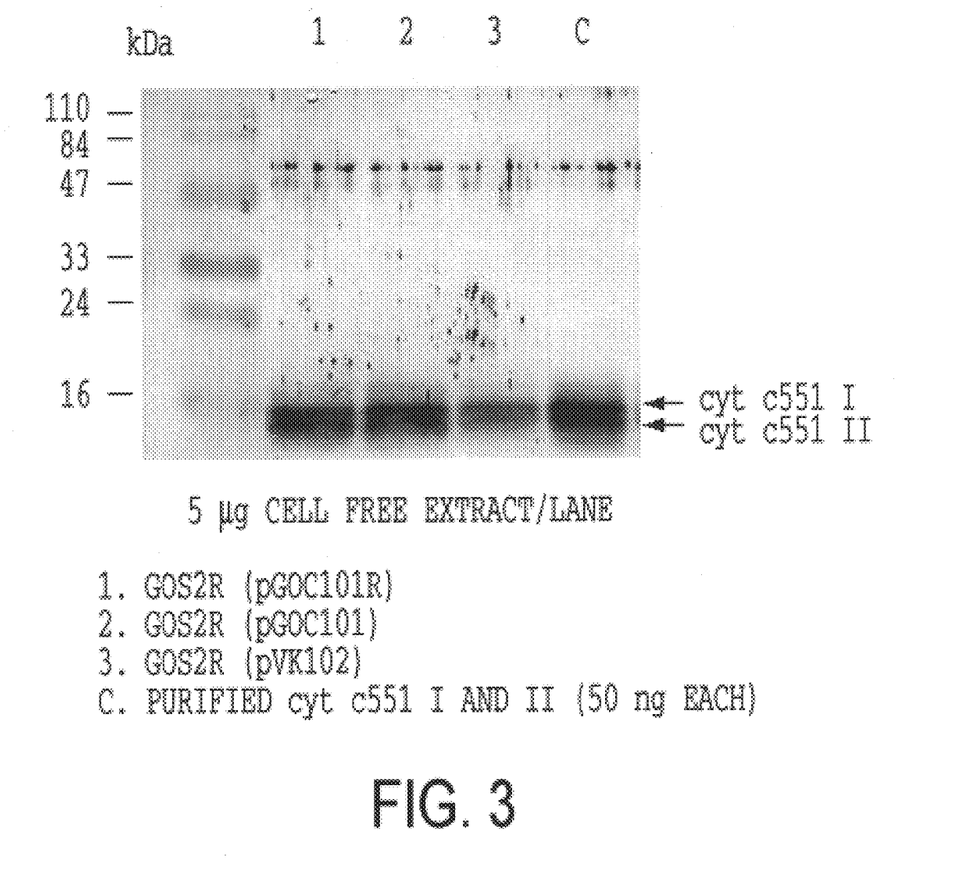
FIG. 3 shows Western-blot analysis of GOS2R carrying the plasmid with cytochrome $c_{551}$ gene.

The plasmids carrying the cytochrome $c_{551}$ gene in pVK100 in both directions (pGOC101 and pGOC 101R)

were introduced into a rifampicin resistant derivative of G. oxydans DSM No. 4025, GOS2R (T. Hoshino et al., European Patent Application No. 9611500.8), by tri-parental conjugal mating method. Cells of GOS2R were cultivated at 30° C. in 10 ml of T medium consisting of 3% Trypticase Soy Broth (Becton Dickinson, Cockeysville, Md., USA) and 0.3% yeast extract (Difco Laboratories, Detroit, Mich.) with 100 μg/ml of rifampicin. Donor strains, E. coli HB11 carrying pGOC101 (Tc'), pGOC101R (Tc') or pVK102 (Km'), and a helper strain, E. coli HB101 carrying pRK2013 (Km'), were grown in LB medium containing appropriate antibiotics overnight at 37° C. These overnight cultures (10 ml of GOS2R culture and 2 ml of E. coli culture) were independently centrifuged and the cell pellets were independently suspended in 2 ml of T medium. One hundred μl each of the cell suspensions were mixed and fifty μl of the mixed cell suspension were spotted onto a nitrocellulose filter placed on the surface of NS2 agar medium described in Example 1-(1). The plate was incubated at 27° C. overnight. The resulting cells were spread onto T agar medium containing 100 μg/ml rifampicin and 3 μg/ml tetracycline (TRT agar plate). The transconjugants thus obtained were purified by streaking on TRT agar plate to remove cells of E. coli and plasmid-free GOS2R. Cells of the transconjugants grown on NS2 agar plates were subjected to Western-blot analysis as described in Example 3-(1). FIG. 3 shows that GOS2R carrying pGOC101 or pGOC101R produced more immunologically-positive proteins than GOS2R carrying pVK102; the amplification ratio seems to be about two-fold.

Plasmids pGOC101 and pGOC102 were introduced into a rifampicin resistant derivative of G. oxydans DSM No. 4025, GORS6-35 (high 2KGA producer from L-sorbose, T. Hoshino et al., European Patent Application No. 9611500.8) by a tri-parental conjugation as described above. The plasmid pGOC101 was introduced at low frequency ($<10^{-8}$ transconjugants per recipient ), while plasmid pGOC102 was introduced at higher frequency (ca. $10^{-4}$ transconjugants per recipient). One of the typical transconjugants carrying pGOC101, GORS6-35 (pGOC101)-1, showed very poor growth and low plasmid stability (50%) as shown in Table 1, suggesting that the presence or expression of the cytochrome $c_{551}$ gene has an inhibitory effect on the growth of the host, which results in amplification of plasmid-free cells during growth. Another transconjugant, GORS6-35 (pGOC101)-2, changed to show good growth and very high plasmid stability (>99%), after several transfers on NS2 agar medium containing 30 μg/ml of tetracycline. This spontaneous alteration in growth seems to have resulted from adaptation of the host to stress by overexpression of cytochrome $c_{551}$. On the contrary, transconjugant carrying pGOC102 showed good growth and high plasmid stability (88%).

The contents of cytochrome $c_{551}$ in the strains grown in production medium containing 10% L-sorbose were quantitatively determined by the reduced minus oxidized difference spectra. The quantitative analysis of cytochrome $c_{551}$ was carried out with a Shimadzu (Kyoto, Japan) UV-2200 spectrophotometer as follows. GORS6-35 derivative strains were cultivated in the production medium containing baker's yeast cells described in Example 1 for 4 days. After removing $CaCO_3$ and baker's yeast cells by centrifugation at 1,000 rpm for 10 min twice, cells were harvested by centrifugation at 8,000 rpm for 10 min. The harvested cells were washed with 50 mM Tris-HCl (pH 7.5) containing 5 mM $MgCl_2$, and resuspended in 5 ml of the same buffer. The cell suspension was passed through a French pressure cell disruptor (1,500 kg/cm²) twice and cell debris was removed by centrifugation at 5,000 rpm for 10 min. The resulting crude extract was ultracentrifuged at 45,000 rpm for 1 hour. The supernatant was used for determining the cytochrome $c_{551}$ content by the reduced minus oxidized difference spectra. For cytochrome oxidation, the sample was treated with 2 mM potassium ferricyanide in 100 mM sodium phosphate buffer (pH 7.0), whereas for reduction it was treated with 0.1% sodium borohydride instead of ferricyanide. The concentration of cytochrome $c_{551}$ (C) in the supernatant is given by the following equation:

$$C=E((A_{551}-A_{541})_{red}-(A_{551}-A_{541})_{ox})$$

E (molar extinction coefficient)=19.1 $mM^{-1}$ $cm^{-1}$

The expression level of cytochrome $c_{551}$ in GORS6-35 (pGOC101)-1, GORS6-35 (pGOC101)-2, GORS6-35 (pGOC102) or GORS6-35 (pVK102) is shown in Table 1. GORS6-35 (pGOC101)-2 and GORS6-35 (pGOC102) expressed 1.6- and 1.3-fold more cytochrome $c_{551}$ than GORS-6-35 (pVK102) did.

TABLE 1

| Strains | Plasmid stability (%) | cytochrome $c_{551}$ content* (n mol/mg soluble protein) |
|---|---|---|
| GORS6-35 (pVK102) | 91 | 0.807 |
| GORS6-35 (pGOC101)-1 | 50 | 0.733 |
| GORS6-35 (pGOC101)-2 | >99 | 1.297 |
| GORS6-35 (pGOC102) | 88 | 1.070 |

*:The content contains those of both cytochrome $c_{551}$ I and II.

Increase of cytochrome $c_{551}$ content in GORS6-35 carrying pGOC102 suggested that the original promoter of cytochrome $c_{551}$ gene possibly exists within the 117 bp upstream its structure gene.

Example 4

2KGA Production from L-sorbose by Cytochrome $c_{551}$-amplified GORS6-35

B. megaterium DSM No. 4026 (European Patent publication 0278477) was inoculated from SCM agar slant (Table 2) into 150 ml of SCM. Into the same SCM seed culture medium, GORS6-35 (pGOC101)-2 or GORS6-35 (pVK102) cells from an agar culture on the NS2 medium containing 30 μg/ml tetracycline, or GORS6-35 or G. oxydans DSM No. 4025 cells from an agar culture on the NS2 medium was inoculated. The seed cultivation was continued until the pH of the broth became between 6.5 and 6.0 at 30° C.; it usually took 15 to 24 hr. The portion (7.5 ml) of the seed broth was inoculated into 50 ml production media (Table 3) in a 500 ml Erlenmeyer flask. These main fermentations were performed at 30° C., 180 rpm on a rotary shaker for 5 days. As shown in Table 4, mixed fermentation using GORS6-35 (pGOC101)-2 resulted in better 2KGA productivity than those by G. oxydans DSM No. 4025, GORS6-35, and GORS6 (pVK102): faster production of 2KGA from 11% L-sorbose, and faster production and higher yield from 14% L-sorbose. The recombinant strain produced 105.1 g/l of 2KGA from 11% L-sorbose in 3 days, and 130.8 and 133.3 g/l from 14% L-sorbose in 4 and 5 days, respectively, while the vector control GORS6-35 (pVK100) produced 96.3 g/l of 2KGA from 11% L-sorbose in 3 days, and 99.9 and 112.6 g/l from 14% in 4 and 5 days, respectively.

TABLE 2

Seed culture medium (SCM)

| Ingredient | Conc. (%) |
|---|---|
| Yeast extract | 0.3 |
| Beef extract | 0.3 |
| Cornsteep liquor | 0.3 |
| Peptone | 1.0 |
| Urea | 0.1 |
| $KH_2PO_4$ | 0.1 |
| $MgSO_4 \cdot 7H_2O$ | 0.02 |
| $CaCO_3$* | 0.1 |
| L-Sorbose | 2.0 |
| pH 7.1 | |

*:$CaCO_3$ is added after pH adjustment.
150 ml of the medium in 500 ml Erlenmeyer flask
For SCM agar slant, 2% of agar was added to the SCM medium

TABLE 3

Production media

| L-Sorbose* | 11% | 14% |
|---|---|---|
| Urea* | 2.4 | 3.1 |
| CSL | 1.6 | 2.0 |
| $MgSO_4 \cdot 7H_2O$ | 0.016 | 0.02 |
| $KH_2PO_4$ | 0.16 | 0.2 |
| $CaCO_3$** | 0.8 | 1.0 |
| pH 6.7 | | |

*:L-Sorbose and urea are separately autoclaved.
**:$CaCO_3$ is added after pH adjustment.
100 ml of the medium in 500-ml Erlenmeyer flask

TABLE 4

| | Sorbose conc. | 2KGA produced (g/L) | | |
|---|---|---|---|---|
| Strain | (w/v %) | 3 days | 4 days | 5 days |
| GORS6-35 (pGOC101)-2 | 11 | 105.1 | 106.2 | |
| | 14 | 103.1 | 130.8 | 133.3 |
| GORS6-35 (pVK102) | 11 | 96.3 | 106.9 | |
| | 14 | 84.1 | 99.9 | 112.6 |
| GORS6-35 | 11 | 95.5 | 104.7 | |
| | 14 | 90.6 | 104.7 | 104.8 |
| DSM No. 4025 | 11 | 102.2 | 106.4 | |
| | 14 | 81.8 | 95.6 | 107.7 |

Example 5

2KGA Production by *P. putida* Transconjugant Carrying Cytochrome $c_{551}$ Gene Together with AADH Genes of *G. oxydans* DSM No. 4025

Four transconjugants of $Nal^r$ *P. putida* ATCC 21812, *P. putida* carrying pSSA102R (vector pVK100 carrying 2.7 kb DNA fragment including Enzyme A gene cloned from *G. oxydans* DSM 4025; the gene codes for the AADH converting L-sorbose to 2KGA; T. Hoshino et al., European Patent Application No. 9611500.8) and pGOC402, *P. putida* carrying pVK102 and pGOC 402, *P. putida* carrying pSSA102R and pMMB22, and *P. putida* carrying pVK102 and pMMB22 were constructed by tri-parental conjugal mating method as described in Example 3-(2). Cells of these four transconjugants maintained on the MB agar medium containing 10 μg/ml of tetracycline and 50 μg/ml of streptomycin were inoculated into 10 ml of MB medium supplemented with 10 μg/ml of tetracycline, 50 μg/ml of streptomycin and 10 mM of IPTG and incubated at 30° C. for 18 hours. The resulting cells were centrifuged and washed with 0.9% NaCl. The resting cell reaction mixture consisting of 20 $OD_{600}$ unit of cells, 4% L-sorbose, 0.3% NaCl, 1% $CaCO_3$, 1 μg/ml of pyrroloquinoline quinone (PQQ) was incubated at 30° C. for 48 hours with shaking. The amount of 2KGA produced by *P. putida* carrying pSSA102R and pGOC402 was 36.4 g/l, whereas those of the other three strains were below 0.5 g/l. Expression of cytochrome $c_{551}$ provided a physiological link from AADH of *G. oxydans* DSM No. 4025 to the electron transport chain of *P. putida*.

Example 6

AADH-cytochrome $c_{551}$ Conjugate

Figure 4:
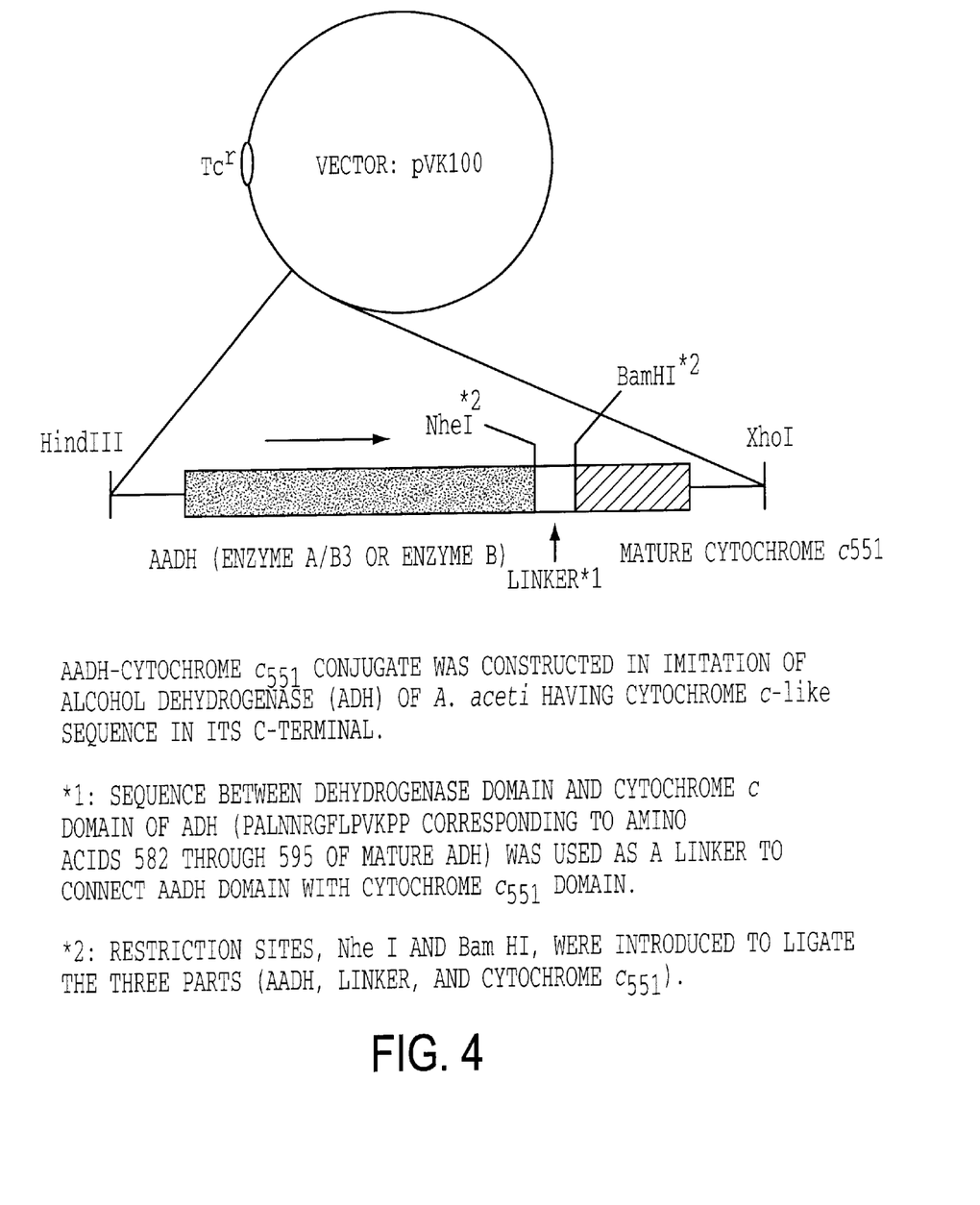
FIG. 4 shows the preparation of the plasmid employed in the expression of alcohol/aldehydee dehydrogenase (AADH)-cytochrome $c_{551}$ conjugate which was constructed in imitation of alcohol dehydrogenase (ADH) of *A. aceti* having cytochrome c-like sequence in its C-terminal. Sequence between dehydrogease domain and cytochrome c domain of ADH (PALNNRGFLPVKPP corresponding to amino acids 582 through 595 of mature ADH) was used as a linker to connect AADH domain with cytochrome $c_{551}$ domain. Restriction sites, Nhe I and Bam HI, were introduced to ligate the three parts (AADH, linker, and cytochrome $c_{551}$).

The plasmids with gene encoding AADH-cytochrome $c_{551}$ conjugates were constructed as illustrated in FIG. 4. Here, Enzyme A/B3 and Enzyme B genes (T. Hoshino et al., European Patent Application No. 9611500.8) were used as AADH genes. The linker between AADH and cytochrome $c_{551}$ was constructed in imitation of ADH of *A. aceti* (Inoue T. et al., J. Bacteriol. 171:3115–3122, 1989). The plasmids were introduced into $Nal^r$ *P. putida* ATCC 21812 and the resulting transconjugant was subjected to the Western-blot analysis with the antibody prepared against AADH or cytochrome $c_{551}$. The analysis showed that constructed conjugates contained both AADH and cytochrome polypeptide in one molecule. The transconjugants carrying Enzyme A/B3-cytochrome $c_{551}$ conjugate gene and Enzyme B-cytochrome $c_{551}$ conjugate gene were used in the resting cell reaction as described in Example 5. As a result, former transconjugants produced 7.8 g/L of 2KGA from 40 g/L of L-sorbose and the latter produced 9.0 g/L of L-sorbose from 40 g/L of D-sorbitol in 40 hr.

We claim:

1. An isolated polynucleotide comprising the DNA sequence defined by SEQ ID NO: 1.

2. An isolated polynucleotide consisting of the DNA sequence defined by SEQ ID NO: 1.

3. An isolated polynucleotide comprising a polynucleotide which encodes the polypeptide defined by SEQ ID NO:2.

4. An isolated polynucleotide consisting of a polynucleotide which encodes the polypeptide defined by SEQ ID NO:2.

5. An isolated polynucleotide comprising a fragment of SEQ ID NO: 1 which encodes a polypeptide having cytochrome c activity.

6. An isolated polynucleotide which encodes a fragment of SEQ ID NO:2 having cytochrome c activity.

7. A recombinant vector suitable for the expression in a pro- or eukaryotic host cell which comprises a polynucleotide recited in any of claims 1–6.

8. A recombinant vector according to claim 7 comprising the polynucleotide of claim 1.

9. A recombinant vector according to claim 7 comprising the polynucleotide of claim 3.

10. A recombinant vector according to claim 7 comprising the polynucleotide of claim 5.

11. A recombinant vector according to claim 7 comprising the polynucleotide of claim 6.

12. A recombinant vector according to claim 7 comprising the polynucleotide of claim 2.

13. A recombinant vector according to claim 7 comprising the polynucleotide of claim 4.

14. A recombinant host cell which is transformed with the polynucleotide defined in any of claims 1–6.

15. A recombinant host cell according to claim 14 comprising the polynucleotide of claim 1.

16. A recombinant host cell according to claim 14 comprising the polynucleotide of claim 3.

17. A recombinant host cell according to claim 14 comprising the polynucleotide of claim 5.

18. A recombinant host cell according to claim 14 comprising the polynucleotide of claim 6.

19. A recombinant host cell according to claim 14 comprising the polynucleotide of claim 2.

20. A recombinant host cell according to claim 14 comprising the polynucleotide of claim 4.

21. A recombinant host cell which is transformed with the recombinant vector defined in any of claims 8–13.

22. A recombinant host cell according to claim 21 comprising the recombinant vector of claim 8.

23. A recombinant host cell according to claim 21 comprising the recombinant vector of claim 9.

24. A recombinant host cell according to claim 21 comprising the recombinant vector of claim 10.

25. A recombinant host cell according to claim 21 comprising the recombinant vector of claim 11.

26. A recombinant host cell according to claim 21 comprising the recombinant vector of claim 12.

27. A recombinant host cell according to claim 21 comprising the recombinant vector of claim 13.

28. A recombinant host cell of claim 21 wherein the host cell is eukaryotic.

29. A recombinant host cell of claim 21 wherein the host cell is mammalian- or plant-derived.

30. A recombinant host cell of claim 21 wherein the host cell is prokaryotic.

31. A recombinant host cell of claim 21 wherein the host cell is bacterial.

32. A recombinant host cell of claim 31 which is selected from the group consisting of *Escherichia coli, Pseudomonas putida, Acetobacter xylinum, Acetobacter pasteurianus, Acetobacter aceti, Acetobacter hansenii,* and *Gluconobactr oxydans*.

33. A recombinant host cell of claim 31, which is a bacterial cell having the identifying characteristics of *Gluconobacter oxydans* DSM No. 4025.

34. A polynucleotide encoding a fusion protein encoded by the sequence defined by SEQ ID NO: 1 operatively linked to a polynucleotide encoding an alcohol aldehyde dehydrogenase polypeptide.

35. A process for producing cytochrome $c_{551}$, which comprises cultivating a recombinant host cell of claim 21 in an appropriate culture medium and recovering the cytochrome $c_{551}$ from the culture medium.

* * * * *

UNITED STATES PATENT AND TRADEMARK OFFICE
CERTIFICATE OF CORRECTION

PATENT NO.    : 6,037,147
DATED         : March 14, 2000
INVENTOR(S)   : Akira Asakura et al.

It is certified that error appears in the above-identified patent and that said Letters Patent is hereby corrected as shown below:

Title page,
Item [75], Inventors", in each of the cities of residence of the inventors, change "Fujisawa" to -- to Fujisawa-shi --, and "Kamakura" to -- Kamakura-shi --.

OTHER PUBLICATIONS,
In the last cited reference, add a -- J. -- after "Inoue I., et al."

Signed and Sealed this

Sixteenth Day of April, 2002

Attest:

JAMES E. ROGAN
Attesting Officer    Director of the United States Patent and Trademark Office

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH:744 base pairs
        (B) TYPE:nucleic acid
        (C) STRANDEDNESS:  double
        (D) TOPOLOGY:   linear (xi) SEQUENCE DESCRIPTION: SEQ ID NO:1:

CAAGGCGGAG TTGTCCGGCA AAGACTGACA TTTCTGTTTG CGGCCGTTAT ATAGGGGCTG      60

CTCGCAGATG TCGGCACCTT GTCCGGCCTG CGACGCAGCA AGGTAAAGGA AGCTAAAATG     120

AAAAACAAAA CCACTCTGGG CGGCGCGCTT GCACTTGCAG CACTGCTGGC CGGAACGACC     180

GGGGCACTGG CGTTCAGCAA CATCGAACGT CCCGCACCGG CCGCTGATAC TGCAGCTACC     240

GAAGAAGCAC CTGCTGCCGC TGCTGGCGCC GCCACTTCGA TCTACGACGG CGTTTACACT     300

GCAGCCCAGG CCGAAGCTGG CCAGGCTGCA TGGATGACCA GCTGCGCAAG CTGCCACGGC     360

CCGACCGCTC GCGGCTCGTC GGGTGGTCCG CGCGTTATCG GCCCTGTCAT CAACAACAAG     420

TATGCTGACA AGCCGCTGCT GGACTACTTC AACTACACCC GCGACAACAT GCCGATGGGC     480

GCGCCTCACT CGTTGAGCGA CGATACCTAT GTTGAAATCG TTGCGTTCAT TCTGCAATCG     540

CACGGCGCAG AGCCGGGCGA GACGGAACTG ACCTCGGACG AAGCGCTGCT CGGCAGCCTG     600

ATGATGGGCC GTAACCCCAA CTAAACGCAG GGTCGCCAAC CGCTTGACGG TAAGCAACCT     660

ACCAGATTGG CCGGCTACGG TCGGCCAATC CTCCTTTACC AACCCTCCAT CCCAAACAAG     720

GTAAAACCTG ATGAAGACGT CGTC                                            744

(2) INFORMATION FOR SEQ ID NO:2:

(i) SEQUENCE CHARACTERISTICS:
        (A) LENGTH:168 residues
        (B) TYPE:amino acid
        (C) TOPOLOGY:   linear (xi) SEQUENCE DESCRIPTION: SEQ ID NO:2:

Met Lys Asn Lys Thr Thr Leu Gly Gly Ala Leu Ala Leu Ala Ala
-25               -20                 -15

Leu Leu Ala Gly Thr Thr Gly Ala Leu Ala Phe Ser Asn Ile Glu
-10                -5                   1                   5

Arg Pro Ala Pro Ala Ala Asp Thr Ala Ala Thr Glu Glu Ala Pro
                10                  15                  20

Ala Ala Ala Ala Gly Ala Ala Thr Ser Ile Tyr Asp Gly Val Tyr
                25                  30                  35

Thr Ala Ala Gln Ala Glu Ala Gly Gln Ala Ala Trp Met Thr Ser
                40                  45                  50

Cys Ala Ser Cys His Gly Pro Thr Ala Arg Gly Ser Ser Gly Gly
                55                  60                  65

Pro Arg Val Ile Gly Pro Val Ile Asn Asn Lys Tyr Ala Asp Lys
                70                  75                  80

Pro Leu Leu Asp Tyr Phe Asn Tyr Thr Arg Asp Asn Met Pro Met
                85                  90                  95

Gly Ala Pro His Ser Leu Ser Asp Asp Thr Tyr Val Glu Ile Val
                100                 105                 110

Ala Phe Ile Leu Gln Ser His Gly Ala Glu Pro Gly Glu Thr Glu
                115                 120                 125

Leu Thr Ser Asp Glu Ala Leu Leu Gly Ser Leu Met Met Gly Arg
                130                 135                 140

Asn Pro Asn

-continued

143

(2) INFORMATION FOR SEQ ID NO:3:

(i) SEQUENCE CHARACTERISTICS:
        (A) LENGTH:52 residues
        (B) TYPE:amino acid
        (C) TOPOLOGY:   linear     (xi) SEQUENCE DESCRIPTION: SEQ ID NO:3:

```
Ala Asp Thr Ala Ala Thr Glu Glu Ala Pro Ala Ala Ala Ala Gly
 1               5                  10                  15

Ala Ala Thr Ser Ile Tyr Asp Gly Val Tyr Thr Ala Ala Gln Ala
                20                  25                  30

Glu Ala Gly Gln Ala Ala Trp Met Thr Ser Xaa Ala Ser Xaa His
                35                  40                  45

Gly Pro Thr Ala Arg Gly Ser
                50      52
```

(2) INFORMATION FOR SEQ ID NO:4:

(i) SEQUENCE CHARACTERISTICS:
        (A) LENGTH:44 residues
        (B) TYPE:amino acid
        (C) TOPOLOGY:   linear     (xi) SEQUENCE DESCRIPTION: SEQ ID NO:4:

```
Gly Pro Arg Val Ile Gly Pro Val Ile Asn Asn Lys Tyr Ala Asp
 1               5                  10                  15

Lys Pro Leu Leu Asp Tyr Phe Asn Tyr Thr Arg Asp Asn Met Pro
                20                  25                  30

Met Gly Ala Pro His Ser Leu Ser Asp Asp Thr Tyr Val Glu
                35                  40              44
```

(2) INFORMATION FOR SEQ ID NO:5:

(i) SEQUENCE CHARACTERISTICS:
        (A) LENGTH:13 residues
        (B) TYPE:amino acid
        (C) TOPOLOGY:   linear     (xi) SEQUENCE DESCRIPTION: SEQ ID NO:5:

```
Ile Leu Gln Ser His Gly Ala Glu Pro Gly Glu Thr Glu
 1               5                  10          13
```

(2) INFORMATION FOR SEQ ID NO:6:

(i) SEQUENCE CHARACTERISTICS:
        (A) LENGTH:50 base pairs
        (B) TYPE:nucleic acid
        (C) STRANDEDNESS:   double
        (D) TOPOLOGY:   linear     (xi) SEQUENCE DESCRIPTION: SEQ ID NO:6:

ATCAACAACA AGTATGCTGA CAAGCCGCTG CTGGACTACT TCAACTACAC    50